US006982075B2

(12) United States Patent
Taut

(10) Patent No.: US 6,982,075 B2
(45) Date of Patent: Jan. 3, 2006

(54) USE OF PULMONARY SURFACTANT

(75) Inventor: Friedemann Taut, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/491,961

(22) PCT Filed: Oct. 10, 2002

(86) PCT No.: PCT/EP02/11325

§ 371 (c)(1),
(2), (4) Date: Apr. 8, 2004

(87) PCT Pub. No.: WO03/033014

PCT Pub. Date: Apr. 24, 2003

(65) Prior Publication Data

US 2004/0247529 A1 Dec. 9, 2004

(30) Foreign Application Priority Data

Oct. 11, 2001 (EP) .................................. 01000531

(51) Int. Cl.
*A61L 9/04* (2006.01)
(52) U.S. Cl. .......................................... 424/45; 514/12
(58) Field of Classification Search ................ 424/145; 514/12; 530/350, 424; 436/186
See application file for complete search history.

(56) References Cited

FOREIGN PATENT DOCUMENTS

| AT | 251449 | 1/1967 |
|---|---|---|
| DE | 32 29 179 A1 | 2/1984 |
| EP | 0 100 910 B1 | 2/1984 |
| EP | 0 110 498 B2 | 6/1984 |
| EP | 0 119 056 B1 | 9/1984 |
| EP | 0 145 005 B1 | 6/1985 |
| EP | 0 251 449 B1 | 1/1988 |
| EP | 0 286 011 B1 | 10/1988 |
| EP | 0 348 967 A2 | 1/1990 |
| EP | 0 368 823 B2 | 5/1990 |
| EP | 0 406 732 B1 | 1/1991 |
| EP | 0 593 094 B1 | 4/1994 |
| WO | 86/03408 | 6/1986 |
| WO | 87/06943 | 11/1987 |
| WO | 88/03170 | 5/1988 |
| WO | 89/04326 | 5/1989 |
| WO | 91/00871 | 1/1991 |
| WO | 91/18015 | 11/1991 |
| WO | 92/22315 | 12/1992 |
| WO | 95/32992 | 12/1995 |
| WO | 97/26863 | 7/1997 |
| WO | 97/35882 | 10/1997 |
| WO | 98/49191 | 11/1998 |
| WO | 01/58423 A1 | 8/2001 |

OTHER PUBLICATIONS

Ghio, A.J. et al. "Synthetic surfactant scavenges oxidants and protects against hyperoxic lung injury", *Surfactant, Oxidants, and Hyperoxic Lung Injury*, American Physiological Society, vol. 77 (3) pp. 1217-1223, 1994.

(Continued)

*Primary Examiner*—Robert A. Wax
*Assistant Examiner*—Robert B. Mondesi
(74) *Attorney, Agent, or Firm*—Nath & Associates PLLC; Joshua B. Goldberg; Sheldon M. McGee

(57) ABSTRACT

The invention describes the novel use of pulmonary surfactant preparations in the artificial respiration of patents with toxic oxygen concentrations.

3 Claims, 1 Drawing Sheet

OTHER PUBLICATIONS

Goerke, Jon "Lung Surfactant", *Biochimica at Biophysica Acta*, Elsevier Scientific Publishing Company, vol. 344 pp. 241-261, 1974.

Gommers, D. et al. "Bronchoalveolar lavage with a diluted surfactant suspension prior to surfactant instillation improves the effectiveness of surfactant therapy in experimental acute respiratory distress syndrome (ARDS)", *Intensive Care Med*, vol. 24 pp. 494-500, 1998.

Häfner, D. et al. "Effects of rSP-C Surfactant on Oxygenation and Histology in a Rat-Lung-Lavage Model of Acute Lung Injury", *Am J Respir Crit Care Med*, vol. 158 pp. 270-278, 1998.

Häfner, D. et al. "Additive Effects on Phosphodiesterase-4 Inhibition on Effects of rSP-C Surfactant", *Am J Respir Crit Care Med*, vol. 161 pp. 1495-1500, 2000.

King, R.J. et al. "Physiological Correlations", *Am J Physiol*, vol. 223 pp. 714-726, 1972.

Lodato, R.F. "Oxygen Toxicity", *Critical Care Clinics*, vol. 6 (3) pp. 749-765, 1990.

Possmayer, F. et al. "Calcium-Protein-Lipid Interactions in Pulmonary Surfactant", *Prog. Resp. Res.*, vol. 18 pp. 112-120, 1984.

Tokieda, K. et al. "Surfactant Protein-B-Deficient Mice Are Susceptible to Hyperoxic Lung Injury", *Am. J. Respir. Cell Mol. Biol.*, vol. 21 pp. 463-472, 1999.

USE OF PULMONARY SURFACTANT

This application is a 371 of PCT/EP02/11325 filed Oct. 10, 2002.

TECHNICAL FIELD OF THE INVENTION

The invention relates to the novel use of pulmonary surfactant preparations in the artificial respiration of patients with toxic oxygen concentrations.

PRIOR ART

It is an urgent aim in the respiration therapy of patients with lung failure to keep the inspiratory oxygen concentration, i.e. oxygen concentration set on the respiration apparatus (FiO2, fraction of inspired oxygen) as low as possible. The risks accompanying an increased (about >0.5) FiO2 are, inter alia:

- formation of higher concentrations of free oxygen radicals O*, which can oxidize protein or lipid structures of the lungs and thus impair them in their function.
- damage to the pulmonary surfactant due to hyperoxia, oxidative processes, inter alia, likewise being involved in the destruction of surfactant constituents (e.g. lipid peroxidation).
- Initiation or intensification of the inflammatory cascade with mediator release and immune cell activation in lung tissue.
- In less aerated areas of the lung there is the danger of absorption atelectases. If the inspiratory gas mixture mostly consists of oxygen, this can be absorbed in the blood so that the gas contents of an affected alveolus strongly decrease. Atelectasis occurs, i.e. the collapse of the alveolus resulting in an increase in the intrapulmonary shunt. (Alveoli supplied with blood, but not aerated, proportionately allow venous blood to pass into the arterial circulation, whereby the oxygen content of the arterial blood can greatly decrease).
- Toxically high oxygen concentrations can induce ARDS (adult respiratory distress syndrome or acute respiratory distress syndrome) per se.
- Disadvantageous fine-tissue changes in the lung are already ascertainable 24 to 48 hours after hyperoxic respiration.

U.S. Pat. No. 4,765,987 describes in Example 5 a study of the efficacy and clinical safety of artificial surfactants in premature infants. A person skilled in the art will know that premature infants are still unable to form any surfactant themselves. The study is not carried out on humans which can form surfactant themselves and have to be respirated with toxic oxygen concentration.

Shamolov et al. (Shamolov V Y et al. (1999) ROSSIISKII VESTNIK PERINATOLOGII I PEDIATRII, volume 44, No. 4, pages 29–34) describes a study of the efficacy in neonates of natural surfactant obtained from amniotic fluid.

For the toxicity of increased oxygen concentrations in the inhaled air, reference may furthermore be made to the summary investigation of Lodato (Lodato, R. F., Critical Care Clinics, 6:749–765).

The physician is therefore always striving to achieve adequate oxygenation of the artificially respirated patient using the lowest possible inspiratory oxygen concentration. Despite the most polished respiration techniques (use of PEEP, other recruitment measures, optimization of the respiration pressures, alteration of the respiratory time conditions), it is often unavoidable, however, in patients with severe lung failure to set the FiO2 above 0.5 up to 1.0.

It is therefore the object of the present invention to make available a medicament which protects the patients from the risks and side effects during respiration with toxic oxygen concentrations.

DESCRIPTION OF THE INVENTION

Surprisingly, it has now been found that after administration of pulmonary surfactant preparations to patents who are respirated artificially with toxic oxygen concentrations, in comparison with respirated patients to whom no pulmonary surfactant preparation has been administered, a significantly faster lowering of the oxygen concentration in the inspiratory respiration gas to concentrations which are less toxic or no longer toxic was achieved while retaining adequate oxygenation of the arterial blood. The risks associated with respiration with toxic oxygen concentrations are decreased and the mortality is lowered. Furthermore, it is to be expected that the respiratory therapy can be ended earlier. The stay of patients in intensive care units can be shortened and costs can thus be saved.

The invention therefore relates to the use of a pulmonary surfactant preparation for the production of medicaments for the prophylaxis or treatment of patients who are artificially respirated and who have a quotient of arterial oxygen partial pressure and inspiratory oxygen concentration (PaO2/FiO2) of 200 mmHg or lower, the oxygen concentration of the gas employed for respiration being 50% by volume or more (FiO2$\geq$0.5).

Toxic oxygen concentrations are understood according to the invention as meaning inspiratory oxygen concentrations of the gas employed for respiration in which the proportion of oxygen is 50% by vol. or more (FiO2$\geq$0.5). Preferably, toxic oxygen concentrations are understood as meaning inspiratory oxygen concentrations of the gas employed for respiration in which the proportion of oxygen is 75% by vol. or more (FiO2$\geq$0.75).

According to the invention, artificial respiration of a patient is understood as meaning the ventilation of the lung brought about by aids. An aid for respiration which may be mentioned by way of example is the respirator, where different forms of respiration known to the person skilled in the art can be used.

Patients with severe lung failure who are respirated are in particular patients having a severe oxygenation disturbance, who have a quotient of arterial oxygen partial pressure (PaO2) and inspiratory oxygen concentration (FiO2) of 200 mmHg or lower (PaO2/FiO 2$\leq$200 mmHg). By way of example, patients with respiratory insufficiency, patients with ARDS, patients with pneumonia, patients with damage to the lungs due to inhaled noxae, patients with cardiogenic pulmonary oedema, patients with anaesthetic respiration, patents with long-term respiration in intensive medicine, patents who are respirated in the course of a resuscitation may be mentioned.

According to the invention, the patients are preferably humans but preferably not premature or newborn babies with IRDS (infant respiratory distress syndrome).

Natural pulmonary surfactant has surface-active properties; it reduces, for example, the surface tension in the pulmonary alveoli. A simple and rapid in vitro test with which the surface activity of pulmonary surfactant can be determined is, for example, the 'Wilhelmy balance' [Goerke, J. Biochim. Biophys. Acta, 344: 241–261 (1974), King R. J. and Clements J. A., Am. J. Physiol. 223: 715–726 (1972)].

This method provides indications of the pulmonary surfactant quality, measured as the activity of a pulmonary surfactant in achieving a surface tension of almost zero mN/m. Another measuring device for determining the surface activity of pulmonary surfactant is the "pulsating bubble surfactometer" [Possmayer F., Yu S. and Weber M., Prog. Resp. Res., Ed. v. Wichert, Vol. 18; 112–120 (1984)].

The activity of a pulmonary surfactant preparation can also be determined by means of in vivo tests, for example such as described by Häfner et al. (D. Häfner et al.: Effects of rSP-C surfactant on oxygenation and histology in a rat lung lavage model of acute lung injury. Am. J. Resp. Crit. Care Med. 1998, 158: 270–278). By the measurement of, for example, the pulmonary compliance, the blood gas exchange or the respiratory pressures needed, indications of the activity of a pulmonary surfactant can be obtained.

Pulmonary surfactant preparations are to be understood according to the invention as meaning the numerous known compositions and their modifications which have the function of natural pulmonary surfactant. The compositions are preferred here which, for example, have activity in the tests described above. Particularly preferred compositions are those which exhibit an increased activity in such a test in comparison with natural or, in particular human, pulmonary surfactant. In this context, they can be compositions, which only contain phospholipids, but also compositions which, apart from the phospholipids, inter alia additionally contain pulmonary surfactant protein. Preferred phospholipids according to the invention are dipalmitoylphosphatidycholine (DPPC), palmitoyloleyl-phosphatidylglycerol (POPG) and/or phosphatidylglycerol (PG). Particularly preferably, the phospholipids are mixture of various phospholipids, in particular mixtures of dipalmitoylphosphatidylcholine (DPPC) and palmitoyloleylphosphatidylglycerol (POPG), preferably in the ratio from 7:3 to 3:7. Commercial products which may be mentioned are CUROSURF® (poractant alfa) (Serono Pharma GmbH, Unterschleißheim), a natural surfactant made from homogenized porcine lungs, SURVANTA® (beractant) (Abbott GmbH, Wiesbaden) and ALVEOFACT® (Boehringer Ingelheim), both extracts of bovine lungs, and also EXOSURF® (Glaxo Wellcome), a synthetic phospholipid containing auxiliaries. Possible pulmonary surfactant proteins are both those obtained from natural sources, such as, for example, pulmonary lavage or extraction from amniotic fluid, and the proteins prepared by genetic engineering or chemical synthesis. According to the invention, the pulmonary surfactant proteins designated by SP-B and SP-C and their modified derivatives are in particular of interest. The amino acid sequences of these pulmonary surfactant proteins, their isolation and preparation by genetic engineering are known (e.g. from WO 86/03408, EP-A-0 251 449, WO 89/04326, WO 87/06943, WO 88/03170, WO 91/00871, EP-A-0 368 823 and EP-A-0 348 967). Modified derivatives of the pulmonary surfactant proteins designated by SP-C, which differ from human SP-C by the replacement of a few amino acids, are described, for example, in WO 91/18015 and WO 95/32992. Particularly to be emphasized in this connection are the recombinant SP-C derivatives which are disclosed in WO 95/32992, in particular those which differ from human SP-C in positions 4 and 5 by the replacement of cysteine by phenylalanine and in the position 32 by the replacement of methionine by isoleucine [designated below as rSP-C (FF/I) or lusupultide (INN)]. Modified derivatives of the pulmonary surfactant proteins should also be understood as meaning those proteins which have an amino acid sequence which is conceived completely independently with respect to their pulmonary surfactant property, such as are described, for example, in EP-A-0 593 094 and WO 92/22315. The polypeptide KL4 (INN:sinapultide) may be preferably mentioned in this connection. The designation pulmonary surfactant protein also comprises, according to the invention, mixtures of different pulmonary surfactant proteins. In EP-B-0 100 910, EP-A-0 110 498, EP-B-0 119 056, EP-B-0 145 005, EP-B-0 286 011, phospholipid compositions with and without pulmonary surfactant proteins are described, which are likewise possible as components of the preparations.

As further constituents which can be present in pulmonary surfactant preparations, fatty acids such as palmitic acid may be mentioned. The pulmonary surfactant preparations can also contain electrolytes such as calcium, magnesium and/or sodium salts (for example calcium chloride, sodium chloride and/or sodium hydrogencarbonate) in order to establish an advantageous viscosity. Preferred preparations according to the invention contain 80 to 95% by weight of phospholipids, 0.5 to 3.0% by weight of pulmonary surfactant proteins, 3 to 15% by weight of fatty acid, preferably palmitic acid, and 0 to 3% by weight of calcium chloride.

The pulmonary surfactant preparations are prepared by processes known per se and familiar to the person skilled in the art, for example as described in WO 95/32992. According to the invention, the pulmonary surfactant preparations are preferably lyophilized and in particular spray-dried pulmonary surfactant preparations. Lyophilized preparations are known, for example, from WO 97/35882, WO 91/00871 and DE 3229179. WO 97/26863 describes a process for the preparation of pulverulent pulmonary surfactant preparations by spray drying. According to the invention, preparations prepared in this manner are preferred.

A further subject of the invention is also a therapeutic process for the prophylaxis or treatment of risks and side effects in the artificial respiration of patients having severe lung failure due to toxic oxygen concentrations. The process comprises administering to the affected patient a therapeutically efficacious and pharmacologically tolerable amount of a pulmonary surfactant preparation. The dosage of the pulmonary surfactant preparations is carried out in the order of magnitude customary for pulmonary surfactant preparations.

The administration of the pulmonary surfactant preparation is carried out in a manner known to the person skilled in the art, preferably by intratracheal instillation (infusion or bolus) of a pulmonary surfactant solution or suspension or in the form of a nebulization of a pulmonary surfactant solution or suspension or by nebulization of pulmonary surfactant powder. Preferably, the preparations according to the invention are dissolved or suspended in a suitable solvent or resuspension medium for administration, in particular if the preparations are present in lyophilized or spray-dried form. Preferably, the suitable resuspension medium is physiological saline solution. It has proven advantageous to administer suspensions or solutions of the preparations according to the invention which contain 12.5 to 100 mg of phospholipids per ml of suspension. Preferably, the preparations according to the invention are administered per administration in an amount such that the amount of phospholipids is between 12.5 and 200 mg per kilogram of body weight. As a rule, the administration is carried out once to three times daily over a period of 1 to 7 days. A process is preferred in which the pulmonary surfactant solution employed contains 0.5 to 2.0 mg of rSP-C (FF/l) per ml of solvent. A process may particularly be mentioned in which the pulmonary surfactant solution employed contains 0.75 to 1.5 mg of rSP-C (FF/l) per ml of solvent. If desired, before the administration of the preparations according to the invention a bronchioalveolar lavage can be carried out, preferably with dilute pulmonary surfactant preparation. Such a procedure is described, for example, in Gommers et al. [Bronchioalviolar lavage with a diluted surfactant suspension prior to surfactant instillation improves the effectiveness of surfactant therapy in experimental acute respiratory distress syndrome (ARDS), Intensive Care Med. 1998, 24: 494–500] and in WO 98/49191.

A further subject of the invention is a commercial product, consisting of a customary secondary packaging, a primary packaging (for example an ampoule) containing a pharmaceutical preparation and, if desired, a pack insert, the pharmaceutical preparation being suitable for the prophylaxis or treatment of risks and side effects in the respiration of patients with toxic oxygen concentrations and the suitability of the pharmaceutical preparation for the prophylaxis or treatment of risks and side effects in respiration with toxic oxygen concentrations being indicated on the secondary packaging or on the pack insert of the commercial product, and the pharmaceutical preparation being a pulmonary surfactant preparation. The secondary packaging, the primary packaging containing the pharmaceutical preparation and the pack insert otherwise correspond to what the person skilled in the art would regard as standard for pharmaceutical preparations of this type. Suitable primary packagings are, for example, ampoules or bottles made of suitable materials such as transparent polyethylene or glass or alternatively suitable administration means such as are customarily employed for the administration of active compounds to the lungs. By way of example, administration means for the nebulization of an active compound solution or suspension or for the nebulization of active compound powder may be mentioned. Preferably, the primary packaging is a glass bottle, which can be closed, for example, by a customary commercial rubber stopper or a septum. A suitable secondary packaging which may be mentioned is, for example, a folded box.

EXAMPLES

A.) Preparation of Pulverulent Pulmonary Surfactant Preparations

The preparation of pulverulent pulmonary surfactant preparations is carried out according to the process described in WO 97/26863:

Example 1

7.0 g of 1,2-dipalmitoyl-3-sn-phosphatidylcholine, 2.5 g of 1-palmitoyl-2-oleoyl-3-sn -phosphatidylglycerol sodium, 205 mg of calcium chloride dihydrate and 250 mg of palmitic acid are dissolved in 300 ml of ethanol/water (85:15) with warming to 60° C., cooled to room temperature and mixed with 350 ml of a solution of rSP-C (FF/l) in chloroform/methanol 9:1 (c=429 mg/l). The resulting solution is spray-dried in a Bücchi B 191 laboratory spray dryer. Spray conditions: drying gas air: inlet temperature 90° C., outlet temperature 52–54° C. A loose powder is obtained.

Example 2

A solution of surfactant prepared from bovine lungs (obtained by extraction and purification steps, such as described, for example, in EP 406732) in chloroform/methanol is spray-dried under the following conditions: Büchi B 191 laboratory spray dryer, drying gas nitrogen: inlet temperature 80° C., outlet temperature 50–52° C. A fine, yellowish powder is obtained.

Example 3

10.95 g of 1,2-dipalmitoyl-3-sn-phosphatidylcholine, 4.6 g of 1-palmitoyl-2-oleoyl-3-sn -phosphatidylglycerol ammonium, 418 mg of calcium chloride dihydrate and 750 mg of palmitic acid are dissolved in 330 ml of 2-propanol/water (85:15) at 50° C. and, after cooling to 30° C., mixed with 620 ml of a solution of rSP-C (FF/l) in isopropanol/water (95:5, c=484 mg/l). The resulting solution is spray dried in a Büchi B 191 laboratory spray dryer, spray conditions: drying gas nitrogen, inlet temperature 100° C., outlet temperature 58–60° C. A colourless powder is obtained.

Example 4

3.74 g (5.1 mmol) of 1,2-dipalmitoyl-3-sn-phosphatidylcholine, 2.81 g (3.7 mmol) of 1-palmitoyl-2-oleoyl-3-sn-phosphatidylcholine, 2.90 g (3.9 mmol) of 1,2-dipalmitoyl -phosphatidyl-3-sn-phosphatidylglycerol sodium, 234 mg of palmitic acid and 279 mg (1.9 mmol) of calcium chloride dihydrate are dissolved in 160 ml of 2-propanol/water (85:15) at 50° C. and, after cooling to 30° C., mixed with 566 ml of a solution of rSP-C (FF/l) in isopropanol/water (92:8, c=330 mg/l) at 30° C. The resulting solution is spray-dried in a Büchi B 191 laboratory spray dryer. Spray conditions: drying gas nitrogen, inlet temperature 90° C., outlet temperature 58–60° C. A colourless powder is obtained.

Example 5

0.5 g of KL4 (INN: sinapultide), 7.125 g of 1,2-dipalmitoyl-3-sn-phosphatidylcholine and 2.43 g of 1-palmitoyl-2-oleoyl-3-sn-phosphatidylglycerol ammonium are dissolved in 500 ml of chloroform/methanol 1:1 with warming to 45° C. and then spray-dried in a Büchi B 191 laboratory spray dryer. Spray conditions: drying gas nitrogen, inlet temperature 85° C., outlet temperature 55° C. A colourless powder is obtained.

Example 6

A solution of phospholipids, palmitic acid and calcium chloride dihydrate obtainable according to Example 1, 3 or 4 is spray-dried—with out addition of a solution of rSP-C (FF/l)—corresponding to the conditions according to Example 1, 3 or 4. A powder is obtained.

B.) Preparation of the Medicaments According to the Invention

Example 7

0.1 to 10 g of the powder obtained according to Example 1 are poured into a bottle having a volume of 100 to 250 ml and the bottle is dosed. The bottle is packed in a suitable folded box together with a pack insert.

Example 8

3 g of the powder obtained according to Example 1 are poured into a bottle having a volume of 66 ml and the bottle is closed. The bottle is packed in a suitable folded box together with a pack insert.

Pharmacological Investigations

In the course of two prospective, multicentre, randomized, double-blind studies with treatment and control groups in patients with ARDS, it was surprisingly seen that in particular those patients who have been respirated with toxic oxygen concentrations (Venticute®, a pulmonary surfactant preparation containing DPPC (diphosphatidylcholine), POPG (palmitoyloleylphosphatidyl glycerol), lusupultide, palmitic acid and calcium chloride was employed) profit from a treatment with a pulmonary surfactant preparation. This finding was seen even at values of the FiO2 from 0.5. In FIG. 1, for illustration, a graph is shown by way of example which shows patients with acute respiratory distress syndrome (ARDS) on account of direct lung damage (pneumonia, aspiration of gastric contents) with extremely high FiO2 values at the start of treatment (FiO2 above 0.8). The inspiratory oxygen fraction (FiO2) was lowered to inspiratory oxygen fractions (or oxygen concentrations) which are less toxic or no longer toxic significantly faster in the group of patients treated with pulmonary surfactant preparation than in the group of untreated patients. The mortality as a gold standard in intensive medicine on day 28 was significantly lower in the group of treated patients (24.1%) than in the control group (37.5%) (FIG. 1). A lowering of the mortality was likewise seen in patients from FiO2 values at the start of treatment of 0.5 or more.

Figure 1:
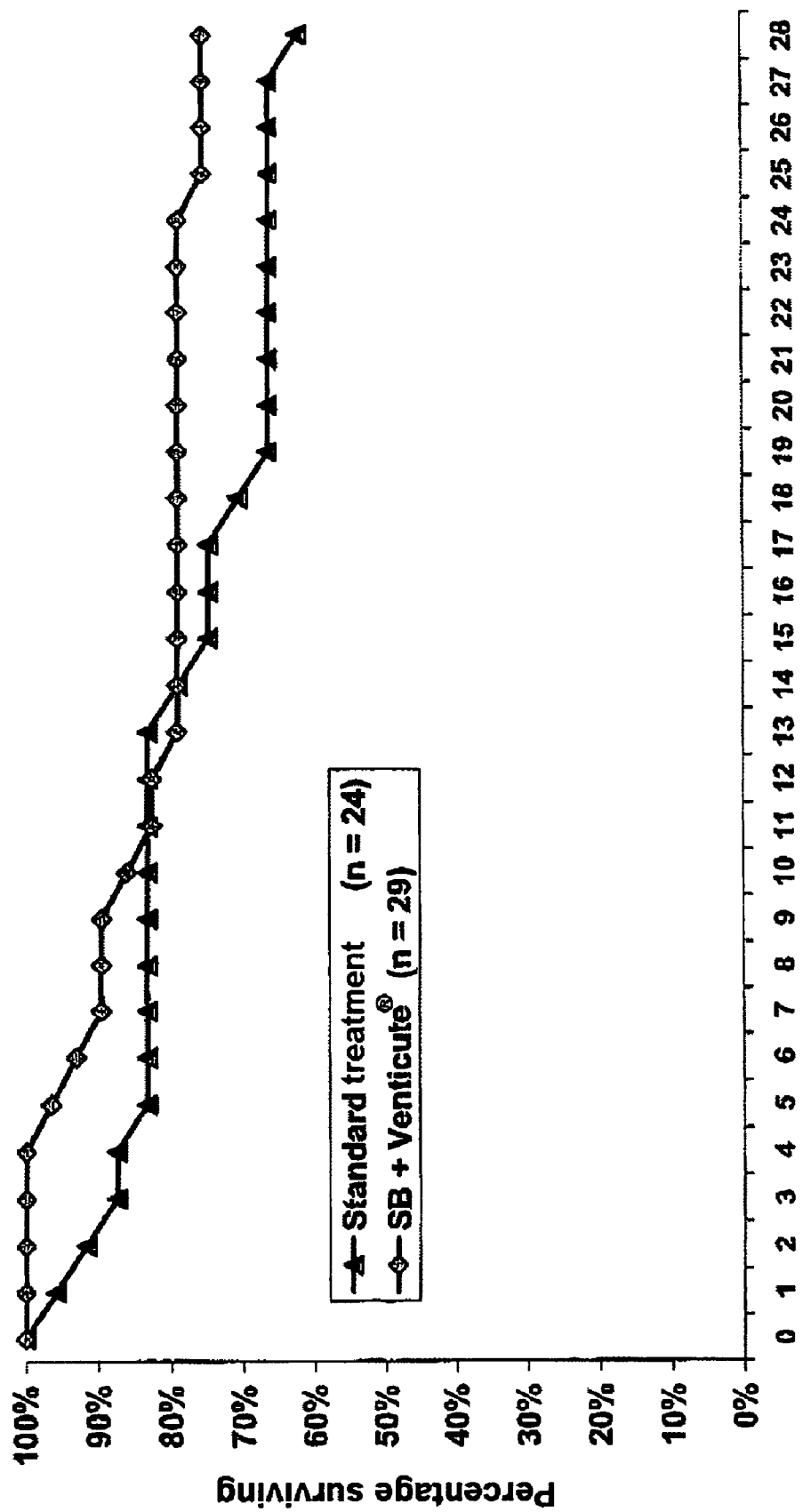
FIG. 1 shows a comparison of the survival rates in two patient groups having acute respiratory distress syndrome, who were respirated artificially with toxic oxygen concentrations, one of the patient groups being administered a pulmonary surfactant preparation (Venticute®).

What is claimed is:

1. A method of treating a patient comprising administering a therapeutically effective amount of a pulmonary surfactant preparation to a patient in order to decrease a risk or side effect of toxic oxygen concentration, wherein the patient is artificially respirated and has a quotient of arterial oxygen partial pressure and inspiratory oxygen concentration (PaO2/FiO2) of 200 mmHg or lower, and wherein the oxygen concentration of the gas employed for respiration is greater than or equal to 50% by volume.

2. The method according to claim 1, wherein the oxygen concentration of the gas employed for respiration is greater than or equal to 75% by volume.

3. The method according to claim 1, wherein the pulmonary surfactant preparation comprises phospholipids along with a pharmaceutically acceptable excipient.

* * * * *